(12) United States Patent
Jonas et al.

(10) Patent No.: US 6,417,188 B1
(45) Date of Patent: Jul. 9, 2002

(54) ARYLALKANOYLPYRIDAZINES

(75) Inventors: Rochus Jonas; Michael Wolf; Franz-Werner Kluxen, all of Darmstadt (DE)

(73) Assignee: Merck Patent Gesellschaft mit beschraenkter Haftung (DE)

( * ) Notice: Subject to any disclaimer, the term of this patent is extended or adjusted under 35 U.S.C. 154(b) by 0 days.

(21) Appl. No.: 09/719,467

(22) PCT Filed: May 7, 1999

(86) PCT No.: PCT/EP99/03151

§ 371 (c)(1),
(2), (4) Date: Dec. 13, 2000

(87) PCT Pub. No.: WO99/65880

PCT Pub. Date: Dec. 23, 1999

(30) Foreign Application Priority Data

Jun. 16, 1998 (DE) .......................... 198 26 841

(51) Int. Cl.[7] .................. A61K 31/50; C07D 237/04
(52) U.S. Cl. .......................... 514/247; 544/224
(58) Field of Search ................... 544/224; 514/247

(56) References Cited

FOREIGN PATENT DOCUMENTS

DE          19632549          2/1998

OTHER PUBLICATIONS

Nicholson et al, *TIPS*, vol. 121, p. 19–27, 1991.*
Nyman et al, Medline Abstract for *Clinical and Experimental Immunology*, vol. 108, p. 415–419, 1997.*
D. W. Combs et la., J. Med. Chem., (1995), vol. 38, pp. 4878–4879.
A.M. Doherty, Current Opinion in Chemical Biology, (1999), vol. 3, pp. 466–473.
V. D. Piaz et al., Eur. J. Med. Chem., (2000), vol. 35, pp. 463–480.
N. Sommer et al., Journal of Neuroimmunology, (1997), vol. 79, pp. 54–61.
P. Secchiero et al., PNAS, (2000), vol. 97, No. 26, pp. 14620–14625.
C. P. Genain et al., Proc. Natl. Acad. Sci. USA, (1995), vol. 92, pp. 3601–3605.

\* cited by examiner

*Primary Examiner*—Richard L. Raymond
(74) *Attorney, Agent, or Firm*—Millen, White, Zelano & Branigan, P.C.

(57) ABSTRACT

Arylalkanoylpyridazine derivatives of the formula I

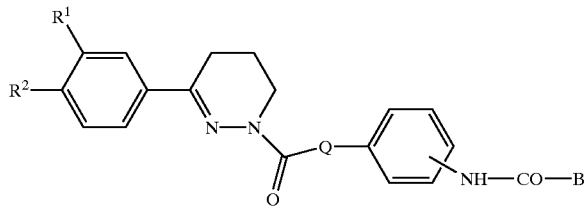

and their physiologically acceptable salts and solvates,
in which $R^1$, $R^2$, Q and B have the meanings indicated in Claim 1, show an inhibition of phosphodiesterase IV and can be employed for the treatment of asthma, chronic bronchitis, atopic dermatitis, psoriasis and other skin diseases, inflammatory diseases, autoimmune disorders, such as, for example, rheumatoid arthritis, multiple sclerosis, Crohn's disease, diabetes mellitus or ulcerative colitis, osteoporosis, transplant rejection reactions, cachexia, tumor growth or tumor metastases, sepsis, memory disorders, atherosclerosis and AIDS.

9 Claims, No Drawings

ARYLALKANOYLPYRIDAZINES

The invention relates to arylalkanoylpyridazine derivatives of the formula I

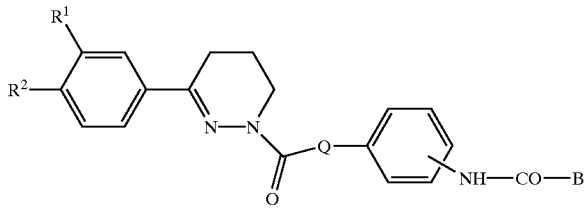

in which
B is a phenyl ring which is unsubstituted or mono- or polysubstituted by $R^3$,
Q is absent or is alkylene having 1–4 C atoms,
$R^1$, $R^2$ each independently of one another are —$OR^4$, —S—$R^4$, —SO—$R^4$, —$SO_2$—$R^4$ or Hal,
$R^1$ and $R^2$ together are also —O—$CH_2$—O—,
$R^3$ is $R^4$, Hal, OH, $OR^4$, OPh, $NO_2$, $NHR^4$, $N(R^4)_2$, $NHCOR^4$, $NHSO_2R^4$ or $NHCOOR^4$,
$R^4$ is A, cycloalkyl having 3–7 C atoms, alkylenecycloalkyl having 5–10 C atoms or alkenyl having 2–8 C atoms,
A is alkyl having 1 to 10 C atoms, which can be substituted by 1 to 5 F and/or Cl atoms and
Hal is F, Cl, Br or I,
and their physiologically acceptable salts and solvates.

1-Benzoyltetrahydropyridazines as progesterone receptor ligands are described, for example, in J. Med. Chem. 38, 4878 (1995). Similar compounds are also disclosed in DE 196 32 549 A1.

The invention was based on the object of finding novel compounds having valuable properties, in particular those which can be used for the production of medicaments.

It has been found that the compounds of the formula I and their salts and solvates have very valuable pharmacological properties together with good tolerability.

In particular, they show a selective inhibition of phosphodiesterase IV, which is accompanied by an intracellular increase in cAMP (N. Sommer et al., Nature Medicine, 1, 244–248 (1995)). The inhibition of PDE IV can be demonstrated, for example, analogously to C. W. Davis in Biochim. Biophys. Acta 797, 354–362 (1984).

The compounds according to the invention can be employed for the treatment of asthmatic disorders. The antiasthmatic action of the PDE IV inhibitors is described, for example, by T. J. Torphy et al. in Thorax, 46, 512–523 (1991) and can be determined, for example, by the method of T. Olsson, Acta allergologica 26, 438–447 (1971).

Since cAMP inhibits osteoclastic cells and stimulates osteogenetic cells (S. Kasugai et al., M 681 and K. Miyamoto, M 682, in Abstracts of the American Society for Bone and Mineral Research 18th Annual Meeting, 1996), the compounds according to the invention can be employed for the treatment of osteoporosis.

The compounds moreover show an antagonistic action on the production of TNF (Tumour Necrosis Factor) and are therefore suitable for the treatment of allergic and inflammatory diseases, autoimmune diseases, such as, for example, rheumatoid arthritis, multiple sclerosis, Crohn's disease., diabetes mellitus or ulcerative colitis, transplant rejection reactions, cachexia and sepsis.

The anti-inflammatory action of the substances according to the invention and their efficacy for the treatment of, for example, autoimmune disorders such as multiple sclerosis or rheumatoid arthritis can be determined analogously to the methods of N. Sommer et al., Nature Medicine 1, 244–248 (1995) or L. Sekut et al., Clin. Exp. Immunol. 100, 126–132 (1995).

The compounds can be employed for the treatment of cachexia. The anti-cachectic action can be tested in TNF-dependent models of cachexia (P. Costelli et al., J. Clin. Invest. 95, 2367ff. (1995); J. M. Argiles et al., Med. Res. Rev. 17, 477ff (1997)).

PDE IV inhibitors can also inhibit the growth of tumour cells and are therefore suitable for tumour therapy (D. Marko et al., Cell Biochem. Biophys. 28, 75ff. (1998)). The action of PDE IV inhibitors in tumour treatment is described, for example, in. WO 95 35 281, WO 95 17 399 or WO 96 00 215.

PDE IV inhibitors can prevent mortality in models of sepsis and are therefore suitable for the therapy of sepsis (W. Fischer et al., Biochem. Pharmacol. 45, 2399ff. (1993)).

They can furthermore be employed for the treatment of memory disorders, atherosclerosis, atopic dermatitis and AIDS.

The action of PDE IV inhibitors in the treatment of asthma, inflammatory disorders, diabetes mellitus, atopic dermatitis, psoriasis, AIDS, cachexia, tumour growth or tumour metastases is described, for example, in EP 77 92 91.

The compounds of the formula I can be employed as pharmaceutical active compounds in human and veterinary medicine. They can furthermore be employed as intermediates for the preparation of further pharmaceutical active compounds.

The invention accordingly relates to the compounds of the formula I and to a process for the preparation of compounds of the formula I according to Claim 1, and of their salts and solvates, characterized in that a compound of the formula II

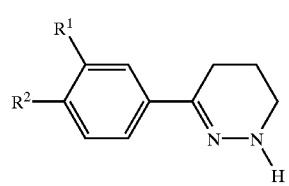

in which
$R^1$ and $R^2$ have the meanings indicated,
is reacted with a compound of the formula III

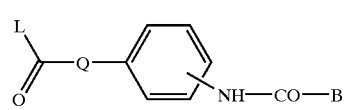

in which
B and Q have the meanings indicated and
L is Cl, Br, OH or a reactive esterified OH group,
or in that a compound of the formula IV

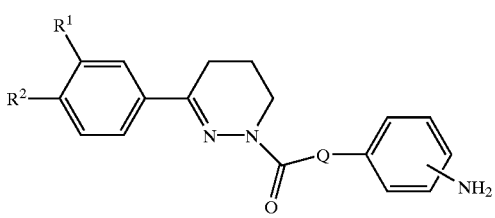

IV in which

R¹, R² and Q have the meanings indicated, is reacted with the compound of the formula V

B—CO—L     V in which

B has the meaning indicated, and

L is Cl, Br, OH or a reactive esterified OH group, and/or in that a basic compound of the formula I is converted into one of its salts by treating with an acid.

Solvates of the compounds of the formula I are understood as meaning adducts of inert solvent molecules to the compounds of the formula I, which are formed as a result of their mutual power of attraction. Solvates are, for example, mono- or dihydrates or alcoholates.

Above and below, the radicals R¹, R², B, Q and L have the meanings indicated in the formulae I, II, III, IV and V, if not expressly stated otherwise.

A is preferably alkyl, furthermore alkyl preferably substituted by 1 to 5 fluorine and/or chlorine atoms.

In the above formulae, alkyl is preferably unbranched and has 1,2,3,4,5,6,7,8,9 or 10 C atoms, preferably 1,2,3,4,5 or 6 C atoms, and is preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl; methyl, ethyl, trifluoromethyl, propyl, isopropyl, butyl, n-pentyl, n-hexyl or n-decyl is particularly preferred.

Cycloalkyl preferably has 3–7 C atoms and is preferably cyclopropyl or cyclobutyl, furthermore preferably cyclopentyl or cyclohexyl, and further also cycloheptyl; cyclopentyl is particularly preferred.

Alkenyl is preferably allyl, 2- or 3-butenyl, isobutenyl, sec-butenyl; 4-pentenyl, isopentenyl or 5-hexenyl is further preferred.

Alkylene is preferably unbranched and is preferably methylene or ethylene, and further preferably propylene or butylene.

Alkylenecycloalkyl preferably has 5–10 C atoms and is preferably methylenecyclopropyl, methylenecyclobutyl, furthermore preferably methylenecyclopentyl, methylenecyclohexyl or methylenecycloheptyl, and further also ethylenecyclopropyl, ethylenecyclobutyl, ethylenecyclopentyl, ethylenecyclohexyl or ethylenecycloheptyl, propylenecyclopentyl, propylenecyclohexyl, butylenecyclopentyl or butylenecyclohexyl.

Hal is preferably F, Cl or Br, but also I.

The radicals R¹ and R² can be identical or different and are in the 3- or 4-position of the phenyl ring. They are, for example, independently of one another hydroxyl, —S—CH₃, —SO—CH₃, —SO₂CH₃, F, Cl, Br or I or together methylenedioxy. Preferably, however, they are each methoxy, ethoxy, propoxy, cyclopentoxy, or else fluoro-, difluoro- or trifluoromethoxy, or 1-fluoro-, 2-fluoro-, 1,2- difluoro-, 2,2-difluoro-, 1,2,2-trifluoro- or 2,2,2-trifluoroethoxy.

The radical R¹ is particularly preferably methoxy, ethoxy, cyclopentoxy or isopropoxy. The radical R² is particularly preferably methoxy or ethoxy.

R³ is preferably R⁴, F, Cl, Br or I, hydroxyl, Oalkyl, OPh, NO₂, alkylamino, cycloalkylamino, dialkylamino, alkylcycloalkylamino, NHCOalkyl, NHCOcycloalkyl, NHSO₂alkyl, NHSO₂cycloalkyl, NHCOOalkyl or NHCOcycloalkyl, where alkyl and cycloalkyl can have one of the meanings indicated beforehand. Particularly preferably, R³ is NO₂, methoxy, ethoxy, propoxy, isopropoxy, butoxy, pentoxy, hexyloxy or decyloxy, Cl or F, NCOOCH₃, NCOOC₂H₅, NSO₂CH₃, NCOCH₃ or NCOCH (CH₃)₂. The radical R³ is particularly preferably in the 3- or 4-position of the phenyl ring.

R⁴ is preferably alkyl, cycloalkyl, alkenyl or alkylenecycloalkyl having the meanings indicated beforehand; alkyl or cycloalkyl is particularly preferred.

The radical B is preferably an unsubstituted phenyl ring or a phenyl ring which is mono- or polysubstituted by R³, where R³ has one of the meanings indicated beforehand. B is further preferably a phenyl, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-N,N-dimethyl-aminophenyl, o-, m- or p-nitrophenyl, o-, m- or p-hydroxyphenyl, o-, m- or p-methoxyphenyl, o-, m- or p-ethoxyphenyl, o-, m- or p-isopropoxyphenyl, o-, m- or p-butoxyphenyl, o-, m- or p-pentoxyphenyl, o-, m- or p-hexyloxyphenyl, o-, m- or p-decyloxyphenyl, o-, m-, p-trifluoromethylphenyl, o-, m- or p-fluorophenyl, o-, m- or p-chlorophenyl, o-, m- or p-bromophenyl, o-, m- or p-acetylaminophenyl, o-, m- or p-isopropylcarbonylaminophenyl, o-, m- or p-methanesulfonylaminophenyl, o, m- or p-ethanesulfonylaminophenyl, o-, m- or p-methoxycarbonylaminophenyl, o-, m- or p-ethoxycarbonylaminophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dimethoxyphenyl.

The radical Q is preferably absent or is preferably alkylene having the preferred meanings indicated beforehand. Q is particularly preferably absent.

It is true of the entire invention that all radicals which occur a number of times can be identical or different, i.e. are independent of one another.

Accordingly, the invention relates in particular to those compounds of the formula I in which at least one of the radicals mentioned has one of the preferred meanings indicated above. Some preferred groups of compounds can be expressed by the following subformulae Ia to Ic, which correspond to the formula I and in which the radicals not designated in greater detail have the meaning indicated in the formula I, but in which in Ia R¹ and R² are each independently of one another OA, Q is absent and B is a phenyl ring which is unsubstituted or substituted by R³;

in Ib

R¹ and R² are each independently of one another OA,

Q is methylene and

B is a phenyl ring which is unsubstituted or substituted by R³;

in Ic

R$^1$ and R$^2$ are together —O—CH$_2$—O—,

Q is absent and

B is a phenyl ring which is unsubstituted or substituted by R$^3$.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. Use can also be made in this case of variants which are known per se, but not mentioned here in greater detail.

In the compounds of the formulae II to IV, R$^1$ and R$^2$ have the meanings indicated, in particular the preferred meanings indicated.

In the compounds of the formulae III and IV, Q is absent or is preferably methylene or ethylene, further preferably propylene or butylene.

B, in the compounds of the formulae III and V, has the preferred meanings indicated, while L is Cl, Br, OH or a reactive esterified OH group.

If L is a reactive esterified OH group, this is preferably alkylsulfonyloxy having 1–6 C atoms (preferably methylsulfonyloxy) or arylsulfonyloxy having 6–10 C atoms (preferably phenyl- or p-tolylsulfonyloxy), and further also 2-naphthalene-sulfonyloxy).

The starting substances, if desired, can also be formed in situ, such that they are not isolated from the reaction mixture but immediately reacted further to give the compounds of the formula I. On the other hand, it is possible to carry out the reaction stepwise.

The compounds of the formula I can preferably be obtained by reacting compounds of the formula II with compounds of the formula III.

The starting substances of the formulae II and III are known in some cases. If they are not known, they can be prepared by methods known per se.

In detail, the reaction of the compounds of the formula II with compounds of the formula III is carried out in the presence or absence of an inert solvent at temperatures between approximately −20 and approximately 150°, preferably between 20 and 100°.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF or dioxane); glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (TMF); nitriles such as acetonitrile; sulfoxides such as dimethyl sulfoxide (DMSO); nitro compounds such as nitromethane or nitrobenzene; esters such as ethyl acetate or mixtures of the solvents mentioned.

Compounds of the formula I can furthermore be obtained by reacting compounds of the formula IV with compounds of the formula V. As a rule, the starting compounds of the formulae IV and V are known. The compounds of the formula IV are known, for example, from DE 196 32 549. If they are not known, they can be prepared by methods known per se. Thus, the preparation of 1-benzoyltetrahydropyridazine, for example, is described in J. Med. Chem. 38, 4878 (1995).

In the compounds of formula V, the radical —CO—L is a preactivated carboxylic acid, preferably a carboxylic acid halide.

The reaction of the compounds of the formula IV with compounds of the formula V takes place under the same conditions, relating to the reaction time, temperature and solvent, as is described for the reaction of the compounds of the formula II with compounds of the formula III.

A base of the formula I can be converted into the associated acid addition salt using an acid, for example by reaction of equivalent amounts of the base and of the acid in an inert solvent such as ethanol and subsequent evaporation. Possible acids for this reaction are in particular those which yield physiologically acceptable salts. Thus, inorganic acids can be used, e.g. sulfuric acid, nitric acid, hydrohalic acids such as hydrochloric acid or hydrobromic acid, phosphoric acids such as orthophosphoric acid, sulfamic acid, and furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, e.g. picrates, can be used for the isolation and/or purification of the compounds of the formula I.

On the other hand, if desired, the free bases of the formula I can also be liberated from their salts with bases (e.g. sodium or potassium hydroxide or sodium or potassium carbonate).

The invention also relates to compounds of the formula I and their physiologically acceptable salts and solvates as medicaments.

The invention also relates to compounds of the formula I and their physiologically acceptable salts and solvates as phosphodiesterase IV inhibitors.

The invention furthermore relates to the use of the compounds of the formula I and/or their physiologically acceptable salts and/or solvates for the production of pharmaceutical preparations, in particular in a non-chemical way. In this connection, they can be brought into a suitable dose form together with at least one solid, liquid and/or semiliquid excipient or auxiliary and, if appropriate, in combination with one or more further active compounds.

The invention furthermore relates to pharmaceutical preparations comprising at least one compound of the formula I and/or one of its physiologically acceptable salts and/or solvates.

These preparations can be used as pharmaceuticals in human or veterinary medicine. Possible excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc and petroleum jelly. In particular, tablets, pills, coated tablets, capsules, powders, granules, syrups, juices or drops are used for oral administration, suppositories are used for rectal administration, solutions, preferably oily or aqueous solutions, and furthermore suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins.

The compounds of the formula I and their physiologically acceptable salts and solvents can be employed in the control of diseases in which an increase in the cAMP (cyclic adenosine monophosphate) level leads to inhibition or prevention of inflammation and to muscle relaxation. The PDE IV inhibitors according to the invention can be particularly useful in the treatment of allergic diseases, asthma, chronic bronchitis, atopic dermatitis, psoriasis and other skin diseases, inflammatory diseases, autoimmune disorders, such as, for example rheumatoid arthritis, multiple sclerosis, Crohn's disease, diabetes mellitus or ulcerative colitis, osteoporosis, transplant rejection reactions, cachexia, tumour growth or tumour metastasis, sepsis, memory disorders, atherosclerosis and AIDS.

In this connection, as a rule the substance according to the invention are preferably administered in doses corresponding to the compound rolipram of between 1 and 500 mg, in particular between 5 and 100 mg per dose unit. The daily dose is preferably between approximately 0.02 and 10 mg/kg of body weight. The specific dose for each patient depends, however, on all sorts of factors, for example on the efficacy of the specific compound employed, on the age, body weight, general state of health, on the sex, on the diet, on the time and route of administration, and on the excretion rate, pharmaceutical combination and on the severity of the particular disorder to which the therapy applies. Oral administration is preferred.

Above and below, all temperatures are indicated in ° C. In the following examples, "customary working up" means: if necessary, water is added, the mixture is adjusted, if necessary, depending on the constitution of the final product, to a pH of between 2 and 10, and extracted with ethyl acetate or dichloromethane, the organic phase is separated off, dried over sodium sulfate and evaporated, and the residue is purified by chromatography on silica gel and/or by crystallization.

EXAMPLE 1

A solution of 1.1 g of 1-(3-aminobenzoyl)-3-(3-ethoxy-4-methoxyphenyl)-1,4,5,6-tetrahydropyridazine, m.p. 180° [obtainable by catalytic hydrogenation of 1-(3-nitrobenzoyl)-3-(3-ethoxy-4-methoxyphenyl)- 1,4,5,6-tetrahydropyridazine, m.p. 173°, in 150 ml of tetrahydrofuran in the presence of 3.5 g of Raney nickel at room temperature] and 0.6 ml of pyridine in 50 ml of acetonitrile is treated with 0.5 g of 4-chlorobenzoyl chloride and stirred for two hours. The solvent is removed and the residue is worked up in the customary manner. After recrystallization, N-(3-(3-ethoxy-4-methoxyphenyl)-1,4,5,6-tetrahydropyridazin-1-ylcarbonyl)phenyl)-4-chlorobenzoyl-3-carboxamide, m.p. 236°, is obtained.

The following are obtained analogously by reaction of 1-(3-aminobenzoyl)-3-(3-ethoxy-4-methoxyphenyl)-1,4,5,6-tetrahydropyridazine with 3-nitrobenzoyl chloride
- N-(3-(3-ethoxy-4-methoxyphenyl)-1,4,5,6-tetrahydropyridazin-1-ylcarbonyl)phenyl)-3-nitrobenzoyl-3-carboxamide, m.p. 160°;

with 4-nitrobenzoyl chloride
- N-(3-(3-ethoxy-4-methoxyphenyl)-1,4,5,6-tetrahydropyridazin-1-ylcarbonyl)phenyl)-4-nitrobenzoyl-3-carboxamide, m.p. 255°;

with 4-methoxybenzoyl chloride
- N-(3-(3-ethoxy-4-methoxyphenyl)-1,4,5,6-tetrahydropyridazin-1-ylcarbonyl)phenyl)-4-methoxybenzoyl-3-carboxamide, m.p. 206°;

with 4-methylbenzoyl chloride
- N-(3-(3-ethoxy-4-methoxyphenyl)-1,4,5,6-tetrahydropyridazin-1-ylcarbonyl)phenyl)-4-methylbenzoyl-3-carboxamide, m.p. 219°;

with benzoyl chloride
- N-(3-(3-ethoxy-4-methoxyphenyl)-1,4,5,6-tetrahydropyridazin-1-ylcarbonyl)phenyl)benzoyl-3-carboxamide, m.p. 203°;

with 3,4-dichlorobenzoyl chloride
- N-(3-(3-ethoxy-4-methoxyphenyl)-1,4,5,6-tetrahydropyridazin-1-ylcarbonyl)phenyl)-3,4-dichlorobenzoyl-3-carboxamide, m.p. 177°;

with 4-trifluoromethylbenzoyl chloride
- N-(3-(3-ethoxy-4-methoxyphenyl)-1,4,5,6-tetrahydropyridazin-1-ylcarbonyl)phenyl)-4-trifluoromethylbenzoyl-3-carboxamide, m.p. 207°;

with 3-chlorobenzoyl chloride
- N-(3-(3-ethoxy-4-methoxyphenyl)-1,4,5,6-tetrahydropyridazin-1-ylcarbonyl)phenyl)-3-chlorobenzoyl-3-carboxamide, m.p. 121°;

with 4-fluorobenzoyl chloride
- N-(3-(3-ethoxy-4-methoxyphenyl)-1,4,5,6-tetrahydropyridazin-1-ylcarbonyl)phenyl)-4-fluorobenzoyl-3-carboxamide, m.p. 236°;

with 4-butoxybenzoyl chloride
- N-(3-(3-ethoxy-4-methoxyphenyl)-1,4,5,6-tetrahydropyridazin-1-ylcarbonyl)phenyl)-4-butoxybenzoyl-3-carboxamide, m.p. 123°;

with 4-pentoxybenzoyl chloride
- N-(3-(3-ethoxy-4-methoxyphenyl)-1,4,5,6-tetrahydropyridazin-1-ylcarbonyl)phenyl)-4-pentoxybenzoyl-3-carboxamide, m.p. 145°;

with 4-ethoxybenzoyl chloride
- N-(3-(3-ethoxy-4-methoxyphenyl)-1,4,5,6-tetrahydropyridazin-1-ylcarbonyl)phenyl)-4-ethoxybenzoyl-3-carboxamide, m.p. 174°;

with 3,4-dimethoxybenzoyl chloride
- N-(3-(3-ethoxy-4-methoxyphenyl)-1,4,5,6-tetrahydropyridazin-1-ylcarbonyl)phenyl)-3,4-dimethoxybenzoyl-3-carboxamide, m.p. 160°;

with 3-methylbenzoyl chloride
- N-(3-(3-ethoxy-4-methoxyphenyl)-1,4,5,6-tetrahydropyridazin-1-ylcarbonyl)phenyl)-3-methylbenzoyl-3-carboxamide, m.p. 115°;

with 3-methoxybenzoyl chloride
- N-(3-(3-ethoxy-4-methoxyphenyl)-1,4,5,6-tetrahydropyridazin-1-ylcarbonyl)phenyl)-3-methoxybenzoyl-3-carboxamide, m.p. 161°.

EXAMPLE 2

A solution of 1.1 g of 1-(4-aminobenzoyl)-3-(3-ethoxy-4-methoxyphenyl)-1,4,5,6-tetrahydropyridazine, m.p. 154° [obtainable by catalytic hydrogenation of 1-(4-nitrobenzoyl)-3-(3-ethoxy-4-methoxyphenyl)-1,4,5,6-tetrahydropyridazine, m.p. 159° C., in 150 ml of tetrahydrofuran in the presence of 3.5 g of Raney nickel at room temperature] and 0.6 ml of pyridine in 50 ml of acetonitrile is treated with 0.5 g of 4-nitrobenzoyl chloride and stirred for two hours. The solvent is removed and the residue is worked up in the customary manner. After recrystallization, N-(3-(3-ethoxy-4-methoxyphenyl)-1,4,5,6-tetrahydropyridazin-1-carbonyl)phenyl)-4-nitrobenzoyl-4-carboxamide, m.p. 233°, is obtained.

The following are obtained analogously by reaction of 1-(4-aminobenzoyl)-3-(3-ethoxy-4-methoxyphenyl)-1,4,5,6-tetrahydropyridazine with 4-methoxybenzoyl chloride N-(3-(3-ethoxy-4-methoxyphenyl)-1,4,5,6-tetrahydropyridazin-1-ylcarbonyl)phenyl)-4-methoxybenzoyl-4-carboxamide, m.p. 201°;

with 4-fluorobenzoyl chloride

N-(3-(3-ethoxy-4-methoxyphenyl)-1,4,5,6-tetrahydropyridazin-1-ylcarbonyl)phenyl)-4-fluorobenzoyl-4-carboxamide, m.p. 193°;

with benzoyl chloride

N-(3-(3-ethoxy-4-methoxyphenyl)-1,4,5,6-tetrahydropyridazin-1-ylcarbonyl)phenyl)benzoyl-4-carboxamide, m.p. 186°;

with 4-chlorobenzoyl chloride

N-(3-(3-ethoxy-4-methoxyphenyl)-1,4,5,6-tetrahydropyridazin-1-ylcarbonyl)phenyl)-4-chlorobenzoyl-4-carboxamide, m.p. 200°;

with 3-nitrobenzoyl chloride

N-(3-(3-ethoxy-4-methoxyphenyl)-1,4,5,6-tetrahydropyridazin-1-ylcarbonyl)phenyl)-3-nitrobenzoyl-4-carboxamide, m.p. 233°.

EXAMPLE 3

A suspension of 4.70 g of 3-(3,4-dimethoxyphenyl)-1,4,5,6-tetrahydropyridazine in 150 ml of THF is treated with 2.24 g of potassium tert-butoxide and stirred for 30 minutes. 5.44 g of 3-benzoylaminobenzoyl chloride are added and the mixture is stirred at room temperature for 10 hours. The solvent is removed and the residue is worked up in the customary manner. N-(3-(3,4-dimethoxyphenyl)-1,4,5,6-tetrahydropyridazin-1-ylcarbonyl)phenyl-3-benzoyl-3-carboxamide, m.p. 196°, is obtained.

The following are obtained analogously by reaction of 3-(3,4-dimethoxyphenyl)-1,4,5,6-tetrahydropyridazine with 3-(3,4-dimethoxybenzoyl)aminobenzoyl chloride N-(3-(3,4-dimethoxyphenyl)-1,4,5,6-tetrahydropyridazin-1-ylcarbonyl)phenyl)-3,4-dimethoxybenzoyl-3-carboxamide, m.p. 183°, with 3-(3-methylbenzoyl)aminobenzoyl chloride N-(3-(3,4-dimethoxyphenyl)-1,4,5,6-tetrahydropyridazin-1-ylcarbonyl)phenyl)-3-methylbenzoyl-3-carboxamide, m.p. 171°, with 3-(3-chlorobenzoyl)aminobenzoyl chloride N-(3-(3,4-dimethoxyphenyl)-1,4,5,6-tetrahydropyridazin-1-ylcarbonyl)phenyl)-3-chlorobenzoyl-3-carboxamide, m.p. 172°, with 3-(4-methoxybenzoyl)aminobenzoyl chloride N-(3-(3,4-dimethoxyphenyl)-1,4,5,6-tetrahydropyridazin-1-ylcarbonyl)phenyl)-4-methoxybenzoyl-3-carboxamide, m.p. 203°.

EXAMPLE 4

Analogously to Example 2, the following are obtained by reaction of 1-(4-aminobenzoyl)-3-(3-isopropoxy-4-methoxyphenyl)-1,4,5,6-tetrahydropyridazine with 4-butoxybenzoyl chloride N-(3-(3-isopropoxy-4-methoxyphenyl)-1,4,5,6-tetrahydropyridazin-1-ylcarbonyl)phenyl)-4-butoxybenzoyl-4-carboxamide, m.p. 161° C.;

with 4-ethoxybenzoyl chloride

N-(3-(3-isopropoxy-4-methoxyphenyl)-1,4,5,6-tetrahydropyridazin-1-ylcarbonyl)phenyl)-4-ethoxybenzoyl-4-carboxamide, m.p. 171° C.;

with benzoyl chloride

N-(3-(3-isopropoxy-4-methoxyphenyl)-1,4,5,6-tetrahydropyridazin-1-ylcarbonyl)phenyl)-benzoyl-4-carboxamide, m.p. 220° C.;

with 3-methylbenzoyl chloride

N-(3-(3-isopropoxy-4-methoxyphenyl)-1,4,5,6-tetrahydropyridazin-1-ylcarbonyl)phenyl)-3-methylbenzoyl-4-carboxamide, m.p. 196° C.;

with 4-cyclopentyloxybenzoyl chloride

N-(3-(3-isopropoxy-4-methoxyphenyl)-1,4,5,6-tetrahydropyridazin-1-ylcarbonyl)phenyl)-4-cyclopentyloxybenzoyl-4-carboxamide, m.p. 163° C.

with 4-isopropoxybenzoyl chloride,

N-(3-(3-isopropoxy-4-methoxyphenyl)-1,4,5,6-tetrahydropyridazin-1-ylcarbonyl)phenyl)-4-isopropoxybenzoyl-4-carboxamide, m.p. 183°;

with 4-propoxybenzoyl chloride,

N-(3-(3-isopropoxy-4-methoxyphenyl)-1,4,5,6-tetrahydropyridazin-1-ylcarbonyl)phenyl)-4-propoxybenzoyl-4-carboxamide, m.p. 171°.

EXAMPLE 5

Analogously to Example 1, the following are obtained by reaction of 1-(3-aminobenzoyl)-3-(3-cyclopentyloxy-4-methoxyphenyl)-1,4,5,6-tetrahydropyridazine with 3-methylbenzoyl chloride N-(3-(3-cyclopentyloxy-4-methoxyphenyl)-1,4,5,6-tetrahydropyridazin-1-ylcarbonyl)phenyl)-3-methylbenzoyl-3-carboxamide, m.p. 144° C.;

with 4-methoxybenzoyl chloride

N-(3-(3-cyclopentyloxy-4-methoxyphenyl)-1,4,5,6-tetrahydropyridazin-1-ylcarbonyl)phenyl)-4-methoxybenzoyl-3-carboxamide, m.p. 194° C.;

with 4-phenylbenzoyl chloride

N-(3-(3-cyclopentyloxy-4-methoxyphenyl)-1,4,5,6-tetrahydropyridazin-1-ylcarbonyl)phenyl)-4-phenylbenzoyl-3-carboxamide, m.p. 140° C.

EXAMPLE 6

Analogously to Example 1, the following are obtained by reaction of 1-(3-aminobenzoyl)-3-(3,4-diethoxyphenyl)-1,4,5,6-tetrahydropyridazine with 4-chlorobenzoyl chloride N-(3-(3,4-diethoxyphenyl)-1,4,5,6-tetrahydropyridazin-1-ylcarbonyl)phenyl)-4-chlorobenzoyl-3-carboxamide, m.p. 152° C.;

with 3-nitrobenzoyl chloride
  N-(3-(3,4-diethoxyphenyl)-1,4,5,6-tetrahydropyridazin-1-ylcarbonyl)phenyl)-3-nitrobenzoyl-3-carboxamide, m.p. 105° C.;
with 4-butoxybenzoyl chloride
  N-(3-(3,4-diethoxyphenyl)-1,4,5,6-tetrahydropyridazin-1-ylcarbonyl)phenyl)-4-butoxybenzoyl-3-carboxamide, m.p. 103° C.;
with 4-ethoxybenzoyl chloride
  N-(3-(3,4-diethoxyphenyl)-1,4,5,6-tetrahydropyridazin-1-ylcarbonyl)phenyl)-4-ethoxybenzoyl-3-carboxamide, m.p. 181° C.

EXAMPLE 7

Analogously to Example 2, the following are obtained by reaction of 1-(4-aminobenzoyl)-3-(3,4-diethoxyphenyl)-1,4,5,6-tetrahydropyridazine
with 4-chlorobenzoyl chloride
  N-(3-(3,4-diethoxyphenyl)-1,4,5,6-tetrahydropyridazin-1-ylcarbonyl)phenyl)-4-chlorobenzoyl-4-carboxamide, m.p. 195° C.;
with 3-nitrobenzoyl chloride
  N-(3-(3,4-diethoxyphenyl)-1,4,5,6-tetrahydropyridazin-1-ylcarbonyl)phenyl)-3-nitrobenzoyl-4-carboxamide, m.p. 218° C.;
with 4-butoxybenzoyl chloride
  N-(3-(3,4-diethoxyphenyl)-1,4,5,6-tetrahydropyridazin-1-ylcarbonyl)phenyl)-4-butoxybenzoyl-4-carboxamide, m.p. 103° C.;
with 4-ethoxybenzoyl chloride
  N-(3-(3,4-diethoxyphenyl)-1,4,5,6-tetrahydropyridazin-1-ylcarbonyl)phenyl)-4-ethoxybenzoyl-4-carboxamide, m.p. 176° C.;
with 4-methoxybenzoyl chloride
  N-(3-(3,4-diethoxyphenyl)-1,4,5,6-tetrahydropyridazin-1-ylcarbonyl)phenyl)-4-methoxybenzoyl-4-carboxamide, m.p. 192° C.

EXAMPLE 8

Analogously to Example 1, the following are obtained by reaction of 1-(3-aminobenzoyl)-3-(3-isopropoxy-4-methoxyphenyl)-1,4,5,6-tetrahydropyridazine
with 4-ethoxybenzoyl chloride
  N-(3-(3-isopropoxy-4-methoxyphenyl)-1,4,5,6-tetrahydropyridazin-1-ylcarbonyl)phenyl)-4-ethoxybenzoyl-3-carboxamide, m.p. 160° C.;
with 4-butoxybenzoyl chloride
  N-(3-(3-isopropoxy-4-methoxyphenyl)-1,4,5,6-tetrahydropyridazin-1-ylcarbonyl)phenyl)-4-butoxybenzoyl-3-carboxamide, m.p. 160° C.;
with 4-methoxybenzoyl chloride
  N-(3-(3-isopropoxy-4-methoxyphenyl)-1,4,5,6-tetrahydropyridazin-1-ylcarbonyl)phenyl)-4-methoxybenzoyl-3-carboxamide, m.p. 161° C.; ps with 4-isopropoxybenzoyl chloride
  N-(3-(3-isopropoxy-4-methoxyphenyl)-1,4,5,6-tetrahydropyridazin-1-ylcarbonyl)phenyl)-4-isopropoxybenzoyl-3-carboxamide, m.p. 168° C.;
with 3-nitrobenzoyl chloride
  N-(3-(3-isopropoxy-4-methoxyphenyl)-1,4,5,6-tetrahydropyridazin-1-ylcarbonyl)phenyl)-3-nitrobenzoyl-3-carboxamide, m.p. 194° C.

EXAMPLE 9

Analogously to Example 1, the following are obtained by reaction of 1-(3-aminobenzoyl)-3-(3,4-dimethoxyphenyl)-1,4,5,6-tetrahydropyridazine
with 4-ethoxybenzoyl chloride
  N-(3,4-dimethoxyphenyl)-1,4,5,6-tetrahydropyridazin-1-ylcarbonyl)phenyl)-4-ethoxybenzoyl-3-carboxamide, m.p. 176° C.;
with 4-butoxybenzoyl chloride
  N-(3,4-dimethoxyphenyl)-1,4,5,6-tetrahydropyridazin-1-ylcarbonyl)phenyl)-4-butoxybenzoyl-3-carboxamide, m.p. 143° C.;
with 4-pentoxybenzoyl chloride
  N-(3,4-dimethoxyphenyl)-1,4,5,6-tetrahydropyridazin-1-ylcarbonyl)phenyl)-4-pentoxybenzoyl-3-carboxamide, m.p. 140° C.;
with 3-propoxybenzoyl chloride
  N-(3,4-dimethoxyphenyl)-1,4,5,6-tetrahydropyridazin-1-ylcarbonyl)phenyl)-3-propoxybenzoyl-3-carboxamide, m.p. 153° C.;
with 4-hexyloxybenzoyl chloride
  N-(3,4-dimethoxyphenyl)-1,4,5,6-tetrahydropyridazin-1-ylcarbonyl)phenyl)-4-hexyloxybenzoyl-3-carboxamide, m.p. 162° C.;
with 4-decyloxybenzoyl chloride
  N-(3,4-dimethoxyphenyl)-1,4,5,6-tetrahydropyridazin-1-ylcarbonyl)phenyl)-4-decyloxybenzoyl-3-carboxamide, m.p. 130° C.

EXAMPLE 10

Analogously to Example 1, the following are obtained by reaction of 1-(3-aminobenzoyl)-3-(3-ethoxy-4-methoxyphenyl)-1,4,5,6-tetrahydropyridazine
with 4-isopropoxybenzoyl chloride
  N-(3-(3-ethoxy-4-methoxyphenyl)-1,4,5,6-tetrahydropyridazin-1-ylcarbonyl)phenyl)-4-isopropoxybenzoyl-3-carboxamide, m.p. 108° C.;
with 3-ethoxybenzoyl chloride
  N-(3-(3-ethoxy-4-methoxyphenyl)-1,4,5,6-tetrahydropyridazin-1-ylcarbonyl)phenyl)-3-ethoxybenzoyl-3-carboxamide, m.p. 142° C.;
with 3-butoxybenzoyl chloride
  N-(3-(3-ethoxy-4-methoxyphenyl)-1,4,5,6-tetrahydropyridazin-1-ylcarbonyl)phenyl)-3-butoxybenzoyl-3-carboxamide, m.p. 144° C.;
with 3-hexyloxybenzoyl chloride
  N-(3-(3-ethoxy-4-methoxyphenyl)-1,4,5,6-tetrahydropyridazin-1-ylcarbonyl)phenyl)-3-hexyloxybenzoyl-3-carboxamide, m.p. 137° C.;
with 4-decyloxybenzoyl chloride
  N-(3-(3-ethoxy-4-methoxyphenyl)-1,4,5,6-tetrahydropyridazin-1-ylcarbonyl)phenyl)-4-decyloxybenzoyl-3-carboxamide, m.p. 123° C.;
with 3-methoxycarbonylaminobenzoyl chloride
  N-(3-(3-ethoxy-4-methoxyphenyl)-1,4,5,6-tetrahydropyridazin-1-ylcarbonyl)phenyl)-3-methoxycarbonylaminobenzoyl-3-carboxamide, m.p. 193° C.;
with 3-ethoxycarbonylaminobenzoyl chloride
  N-(3-(3-ethoxy-4-methoxyphenyl)-1,4,5,6-tetrahydropyridazin-1-ylcarbonyl)phenyl)-3-ethoxycarbonylaminobenzoyl-3-carboxamide, m.p. 221° C.;

with 3-methanesulfonylaminobenzoyl chloride
  N-(3-(3-ethoxy-4-methoxyphenyl)-1,4,5,6-tetrahydropyridazin-1-ylcarbonyl)phenyl)-3-methanesulfonylaminobenzoyl-3-carboxamide, m.p. 174° C.;
with 4-methoxycarbonylaminobenzoyl chloride
  N-(3-(3-ethoxy-4-methoxyphenyl)-1,4,5,6-tetrahydropyridazin-1-ylcarbonyl)phenyl)-4-methoxycarbonylaminobenzoyl-3-carboxamide, m.p. is 234° C.;
with 4-ethoxycarbonylaminobenzoyl chloride
  N-(3-(3-ethoxy-4-methoxyphenyl)-1,4,5,6-tetrahydropyridazin-1-ylcarbonyl)phenyl)-4-ethoxycarbonylaminobenzoyl-3-carboxamide, m.p. 221° C.;
with 4-acetylaminobenzoyl chloride
  N-(3-(3-ethoxy-4-methoxyphenyl)-1,4,5,6-tetrahydropyridazin-1-ylcarbonyl)phenyl)-4-acetylaminobenzoyl-3-carboxamide, m.p. 244° C.

EXAMPLE 11

Analogously to Example 2, the following are obtained by reaction of 1-(4-aminobenzoyl)-3-(3-ethoxy-4-methoxyphenyl)-1,4,5,6-tetrahydropyridazine
with 4-acetylaminobenzoyl chloride
  N-(3-(3-ethoxy-4-methoxyphenyl)-1,4,5,6-tetrahydropyridazin-1-ylcarbonyl)phenyl)-4-acetylaminobenzoyl-4-carboxamide, m.p. >266° C.;
with 4-isopropylcarbonylaminobenzoyl chloride
  N-(3-(3-ethoxy-4-methoxyphenyl)-1,4,5,6-tetrahydropyridazin-1-ylcarbonyl)phenyl)-4-isopropylcarbonylaminobenzoyl-4-carboxamide, m.p.>260° C.;
with 4-methoxycarbonylaminobenzoyl chloride
  N-(3-(3-ethoxy-4-methoxyphenyl)-1,4,5,6-tetrahydropyridazin-1-ylcarbonyl)phenyl)-4-methoxycarbonylaminobenzoyl-4-carboxamide, m.p. 275° C.;
with 4-ethoxycarbonylaminobenzoyl chloride
  N-(3-(3-ethoxy-4-methoxyphenyl)-1,4,5,6-tetrahydropyridazin-1-ylcarbonyl)phenyl)-4-ethoxycarbonylaminobenzoyl-4-carboxamide, m.p. 246° C.;
with 4-methanesulfonylaminobenzoyl chloride
  N-(3-(3-ethoxy-4-methoxyphenyl)-1,4,5,6-tetrahydropyridazin-1-ylcarbonyl)phenyl)-4-methanesulfonylaminobenzoyl-4-carboxamide, m.p.>260° C.

EXAMPLE 12

Analogously to Example 1, the following are obtained by reaction of 1-(3-aminobenzoyl)-3-(3,4-diethoxyphenyl)-1,4,5,6-tetrahydropyridazine
with 4-pentoxybenzoyl chloride
  N-(3-(3,4-diethoxyphenyl)-1,4,5,6-tetrahydropyridazin-1-ylcarbonyl)phenyl)-4-pentoxybenzoyl-3-carboxamide, m.p. 145° C.;
with 3-propoxybenzoyl chloride
  N-(3-(3,4-diethoxyphenyl)-1,4,5,6-tetrahydropyridazin-1-ylcarbonyl)phenyl)-3-propoxybenzoyl-3-carboxamide, m.p. 112° C.;
with 3-butoxybenzoyl chloride
  N-(3-(3,4-diethoxyphenyl)-1,4,5,6-tetrahydropyridazin-1-ylcarbonyl)phenyl)-3-butoxybenzoyl-3-carboxamide, m.p. 120° C.;
with 3-hexyloxybenzoyl chloride
  N-(3-(3,4-diethoxyphenyl)-1,4,5,6-tetrahydropyridazin-1-ylcarbonyl)phenyl)-3-hexyloxybenzoyl-3-carboxamide, m.p. 151° C.;
with 3-ethoxybenzoyl chloride
  N-(3-(3,4-diethoxyphenyl)-1,4,5,6-tetrahydropyridazin-1-ylcarbonyl)phenyl)-3-ethoxybenzoyl-3-carboxamide, m.p. 141° C.

The following examples relate to pharmaceutical preparations:

Example A

Injection Vials

A solution of 100 g of an active compound of the formula I and 5 g of disodium hydrogen phosphate is adjusted to pH 6.5 in 3 l of double-distilled water using 2 N hydrochloric acid, sterile-filtered, dispensed into injection vials, lyophilized under sterile conditions and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution of 1 g of an active compound of the formula I, 9.38 g of $NaH_2PO_4.2 H_2O$, 28.48 g of $Na_2HPO_4.12 H_2O$ and 0.1 g of benzalkonium chloride in 940 ml of double-distilled water is prepared. It is adjusted to pH 6.8, made up to 1 l and sterilized by irradiation. This solution can be used in the form of eye drops.

Example D

Ointment 500 mg of an active compound of the formula I is mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner, such that each tablet contains 10 mg of active compound.

Example F

Coated Tablets

Analogously to Example E, tablets are pressed which are then coated in a customary manner with a coating of sucrose, potato starch, talc, tragacanth and colourant.

Example G

Capsules 2 kg of active compound of the formula I are dispensed into hard gelatine capsules in a customary manner such that each capsule contains 20 mg of the active compound.

Example H

Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

Example I

Inhalation Spray 14 g of active compound of the formula I are dissolved in 10 l of isotonic NaCl solution and the solution is dispensed into commercially available spray vessels having a pump mechanism. The solution can be sprayed into the mouth or nose. One puff of spray (approximately 0.1 ml) corresponds to a dose of approximately 0.14 mg.

What is claimed is:

1. Compounds of the formula I

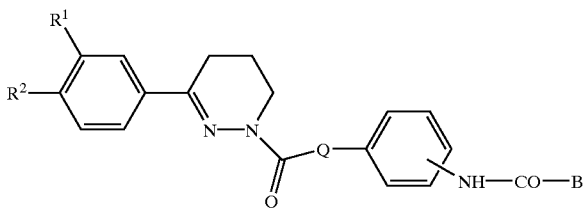

in which
- B is a phenyl ring which is unsubstituted or mono- or polysubstituted by $R^3$,
- Q is absent or is alkylene having 1–4 C atoms,
- $R^1$, $R^2$ each independently of one another are —$OR^4$, —S—$R^4$, —SO—$R^4$, —$SO_2$—$R^4$, or Hal,
- $R^1$ and $R^2$ together are also —O—$CH_2$—O—,
- $R^3$ is $R^4$, Hal, OH, $OR^4$, OPh, $NO_2$, $NHR^4$, $N(R^4)_2$, $NHCOR^4$, $NHSO_2R^4$ or $NHCOOR^4$,
- $R^4$ is A, cycloalkyl having 3–7 C atoms, alkylenecycloalkyl having 5–10 C atoms or alkenyl having 2–8 C atoms,
- A is alkyl having 1 to 10 C atoms, which can be substituted by 1 to 5 F and/or Cl atoms and
- Hal is F, Cl, Br or I, or a physiologically active salt or solvate thereof.

2. Compounds of the formula I according to claim 1, which are
   (a) N-(3-(3-ethoxy-4-methoxyphenyl)-1,4,5,6-tetrahydropyridazin-1-ylcarbonyl)phenyl)-4-chlorobenzoyl-3-carboxamide;
   (b) N-(3-(3-ethoxy-4-methoxyphenyl)-1,4,5,6-tetrahydropyridazin-1-ylcarbonyl)phenyl)-4-pentoxybenzoyl-3-carboxamide;
   (c) N-(3-(3-ethoxy-4-methoxyphenyl)-1,4,5,6-tetrahydropyridazin-1-ylcarbonyl)phenyl)-4-methoxybenzoyl-3-carboxamide; or
   (d) N-(3-(3-ethoxy-4-methoxyphenyl)-1,4,5,6-tetrahydropyridazin-1-ylcarbonyl)phenyl)-3-chlorobenzoyl-3-carboxamide.

3. Process for the preparation of compounds of the formula I according to claim 1 or a salt thereof, wherein a compound of the formula II

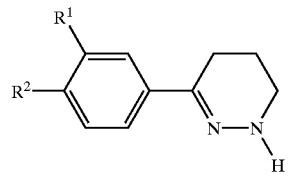

is reacted with a compound of the formula III

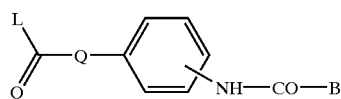

in which
- L is Cl, Br, OH or a reactive esterified OH group, or a compound of the formula IV

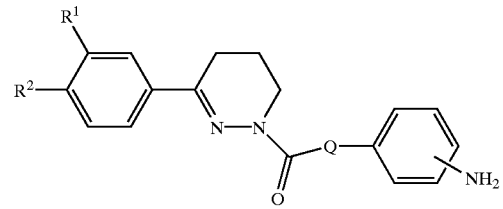

is reacted with the compound of the formula V

in which
- L is Cl, Br, OH or a reactive esterified OH group, and/or in that a basic compound of the formula I is converted into one of its salts by treating with an acid.

4. A pharmaceutical composition comprising at least one compound of the formula I according to claim 1 and/or one of its physiologically acceptable salts and/or one of its solvates.

5. Process for the production of pharmaceutical preparations, wherein a compound of the formula I according to claim 1 and/or one of its physiologically acceptable salts and/or one of its solvates is brought into a suitable dose form together with at least one solid, liquid or semiliquid excipient or auxiliary.

6. A method for inhibiting PDE IV in a host in need thereof, comprising administering an effective amount of a compound according to claim 1.

7. A method for treating asthma, atopic dermatitis, psoriasis, an inflammatory disease, an autoimmune disorder, osteoporosis, cachexia, tumor growth, tumor metastasis, sepsis or AIDS comprising administering an effective amount of a compound according to claim 1.

8. A method for treating rheumatoid arthritis, multiple sclerosis, Crohn's disease, diabetes mellitus or ulcerative colitis comprising administering an effective amount of a compound according to claim 1.

9. A method for treating an allergic disease, chronic bronchitis, skin disease, transplant rejection reaction, a memory disorder or atherosclerosis comprising administering an effective amount of a compound according to claim 1.

* * * * *